(12) United States Patent
Fröderberg et al.

(10) Patent No.: US 8,431,085 B2
(45) Date of Patent: Apr. 30, 2013

(54) APPARATUS FOR TREATING MATERIAL COMPRISING PRESSURE VESSEL WITH DRUM ROTATABLE ARRANGED INSIDE

(75) Inventors: Per-Arne Fröderberg, Borlänge (SE); Melvin R. Madeley, Staffordshire (GB); Anna-Lena Seedhill, Scottsdale, AZ (US)

(73) Assignee: Sanciflex AB, Sorunda (SE)

( * ) Notice: Subject to any disclaimer, the term of this patent is extended or adjusted under 35 U.S.C. 154(b) by 638 days.

(21) Appl. No.: 12/613,780

(22) Filed: Nov. 6, 2009

(65) Prior Publication Data

US 2010/0055010 A1    Mar. 4, 2010

(30) Foreign Application Priority Data

May 7, 2007 (WO) .................. PCT/SE2007/050307

(51) Int. Cl.
- *A61L 9/00* (2006.01)
- *B08B 3/00* (2006.01)
- *B02C 17/00* (2006.01)
- *B07B 13/05* (2006.01)
- *A62D 3/00* (2007.01)

(52) U.S. Cl.
USPC ........... 422/295; 422/297; 422/298; 422/299; 422/300; 422/305; 422/307; 134/105; 241/16; 241/38; 241/DIG. 38; 588/234; 209/687; 209/930

(58) Field of Classification Search ............... 422/26–28, 422/295, 297–300, 305, 307; 134/61, 65, 134/105; 241/16, 38, 23–24, DIG. 38; 588/234; 209/687, 930, 11

See application file for complete search history.

(56) References Cited

U.S. PATENT DOCUMENTS

| | | | |
|---|---|---|---|
| 4,264,741 A | | 4/1981 | Friedman |
| 4,974,781 A | * | 12/1990 | Placzek ........................... 241/17 |
| 5,119,994 A | * | 6/1992 | Placzek ........................... 241/17 |
| 5,427,650 A | | 6/1995 | Holloway |
| 5,746,987 A | * | 5/1998 | Aulbaugh et al. ............ 422/610 |
| 7,745,208 B2 | | 6/2010 | Noll |

FOREIGN PATENT DOCUMENTS

| | | |
|---|---|---|
| AT | 384009 | 2/1987 |
| EP | 0575005 | 12/1993 |
| EP | 1118706 | 7/2001 |
| WO | 2006/015423 | 2/2006 |
| WO | 2006/056768 | 6/2010 |

* cited by examiner

*Primary Examiner* — Jill Warden
*Assistant Examiner* — Monzer Chorbaji
(74) *Attorney, Agent, or Firm* — Bryan Cave LLP

(57) ABSTRACT

An apparatus for treating material includes a pressure vessel and an agitation device for agitating the material received in the pressure vessel. The agitation device may include a drum which may be rotatably arranged inside the pressure vessel and which has an inner space for receiving the material that is introduced into the pressure vessel. The agitation device may include one or more agitation blades mounted in the drum so as to act on the material received in the inner space of the drum as the drum rotates in relation to the pressure vessel. A drive mechanism may rotate the drum in relation to the pressure vessel. Waste, such as garbage, may be treated with steam and pressure using the apparatus.

20 Claims, 3 Drawing Sheets

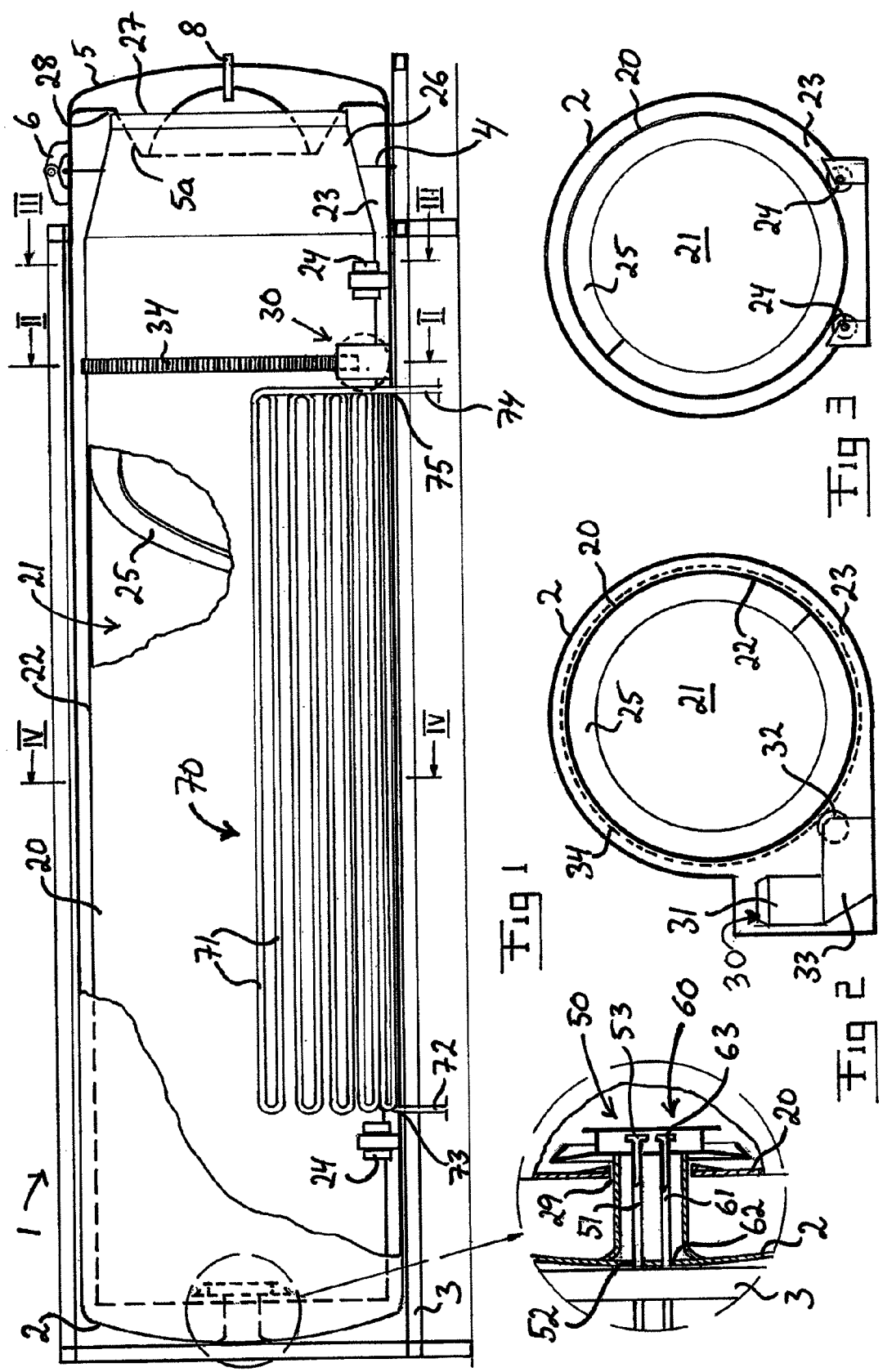

APPARATUS FOR TREATING MATERIAL COMPRISING PRESSURE VESSEL WITH DRUM ROTATABLE ARRANGED INSIDE

RELATED PATENT APPLICATIONS

This patent application claims priority to International Patent Application Number PCT/SE2007/050307, filed on 7 May, 2007, having the same title and inventors, the contents of which are incorporated herein by reference.

FIELD OF THE INVENTION

The present invention relates to material treatment apparatuses and methods. Particular embodiments relate to apparatuses and methods for treating household waste or garbage, for treating material with heat, pressure, or both, or a combination thereof.

BACKGROUND OF THE INVENTION

It is known to process waste, such as household waste, in an autoclave, in which the waste is subjected to steam at suitable pressure and temperature so as to thereby sterilize the waste and make it safe to handle during the subsequent treatment thereof, for example. The processing of waste in an autoclave will also give other benefits. As an example, organic material within the waste is broken down by the treatment in the autoclave to form a mass of small cellulose particles. Furthermore, plastic objects may be reduced in size during the processing in the autoclave and labels and printings on packages of metal, glass and plastic may be removed. The mass of cellulose particles may be used for different applications and the remaining waste leaving the autoclave can be sorted in order to remove recyclable matter, as examples.

A waste treatment autoclave is previously known from WO 2006/056768 A2, for example. This autoclave comprises a pressure vessel which is rotatable about its longitudinal axis in order to agitate waste received inside the pressure vessel. This known autoclave also comprises an internal helix structure projecting from the inner side of the pressure vessel so as to act on waste received in the pressure vessel as the pressure vessel rotates.

Needs and potential for benefit exist for adaptations and improvements to certain apparatuses and methods for treating materials that may be used, for example, for treating waste or garbage. Problems that may be overcome by such adaptations and improvements include increasing the useful life of components, reducing cost of manufacture, increasing effectiveness, simplifying operation, facilitating formation of a seal on pressure vessels, and the like. Room for improvement exists over the prior art in these and other areas that may be apparent to a person of ordinary skill in the art having studied this document.

SUMMARY OF PARTICULAR EMBODIMENTS OF THE INVENTION

Various embodiments provide, for example, as an object or benefit, that they partially or fully address or satisfy one or more of the needs, potential areas for benefit, or opportunities for improvement described herein, or known in the art, as examples. Some embodiments of the invention provide, among other things, various apparatuses and methods for treating materials, for example, that increase the useful life of components, reduce cost of manufacture, increase effectiveness, simplify operation, facilitate formation of a seal on pressure vessels, and the like.

Various embodiments provide, for example, as an object or benefit, that they partially or fully treat material, for instance material in the form of waste, under agitation, for instance, at a pressure above or below that of the atmosphere, or a combination thereof, as examples. Benefits of various embodiments of the invention exist over the prior art in these and other areas that may be apparent to a person of ordinary skill in the art having studied this document.

In a number of embodiments, the desired agitation of material treated in the pressure vessel is accomplished in an efficient and simple manner without having to rotate the pressure vessel itself. The pressure vessel may consequently be fixed, in various embodiments, which offers several advantages as compared to a rotatably arranged pressure vessel. It is for instance much easier to accomplish a secure and pressure-tight clamping of a door to a fixed pressure vessel as compared to a rotary pressure vessel, owing to the fact that the clamps clamping the door to a fixed pressure vessel do not have to be rotatably arranged. In certain embodiments, this facilitates the use of robust and reliable clamps, which for instance may be hydraulically, pneumatically or electrically actuated, as examples. Furthermore, suitable inlet conduits may be more-easily mounted for steam, compressed air, etc., in a reliable and pressure-tight manner to a fixed pressure vessel as compared to a rotary pressure vessel. The use of a fixed pressure vessel as compared to a rotary pressure vessel may also make it easier to mount suitable heating members to the pressure vessel in order to achieve heating of material received in the pressure vessel, as another example.

In some embodiments, the drum has an open end projecting through an opening of the pressure vessel, and the door may be arranged to close the opening of the pressure vessel as well as the open end of the drum. This open end of the drum may extend beyond the associated opening of the pressure vessel, so material may be prevented from falling down into the interspace between the pressure vessel and the drum, in some embodiments, when being fed into or discharged out of the inner space of the drum. Further advantageous features of certain embodiments of the invention are described in the following description.

In specific embodiments, the invention provides various apparatuses for treating material, An apparatus may include a pressure vessel having at least one opening to feed the material into the pressure vessel, a door to close the opening of the pressure vessel, a pressure regulating system to change pressure inside the pressure vessel, and an agitation device to agitate material received in the pressure vessel. In a number of embodiments, the agitation device may include a drum, which may be rotatably arranged inside the pressure vessel, for example, so as to be rotatable in relation to the pressure vessel. Further, in various embodiments, the drum may have an inner space for receiving material that is introduced into the pressure vessel via the opening of the pressure vessel, a cylindrical wall, for instance, designed to prevent material received in the inner space of the drum from falling into an interspace between the drum and the pressure vessel as the drum rotates in relation to the pressure vessel, or both, for example. Additionally, in certain embodiments, the agitation device may include at least one agitation blade mounted on an inner side of the cylindrical wall of the drum, for instance, so as to act on material received in the inner space of the drum as the drum rotates in relation to the pressure vessel. Moreover, in some embodiments, the apparatus may further include a drive mechanism for rotating the drum in relation to the pressure vessel, for example. In some such embodiments, at least one agitation blade extends in a helical path along the cylindrical wall of the drum, for instance, or the at least one agitation blade may include a screw-shaped blade, for example. In particular embodiments, the at least one agitation blade may be arranged to move material received in the inner space of the drum forward away from the opening of the pressure vessel when the drum is rotated by the drive mechanism in a first direction, and the at least one agitation blade may be arranged to move material received in the inner space of the drum backward towards the opening of the pressure vessel when the drum is rotated by the drive mechanism in a second direction opposite the first direction, for instance. In addition, in certain embodiments, the drum has a longitudinal axis and the drum may be arranged with the longitudinal axis extending in a horizontal or at least approximately-horizontal direction. Furthermore, in some embodiments, the drum has an open end projecting through the opening of the pressure vessel, and the door may be arranged to close the opening of the pressure vessel as well as the open end of the drum. Moreover, in some embodiments, the door may have a part arranged to extend into the opening at the open end of the drum when the door is closed, for example.

In various embodiments, the apparatus may include hydraulically, pneumatically or electrically actuated clamps, as examples, for clamping the door to the pressure vessel when the door is closed. Further, in some embodiments, the apparatus may include a heater, for instance, to heat material received in the inner space of the drum. In particular embodiments, the heater may include at least one heating member arranged in the interspace between the drum and the pressure vessel, for example. Further still, in some embodiments, the apparatus may include a steam supply system to supply steam into the inner space of the drum, for example, In certain embodiments, the steam supply system may include a steam supply conduit, for instance, extending into the inner space of the drum through an opening at the end of the drum facing away from the opening of the pressure vessel, for example. In a number of embodiments, the drum rests on rollers which may be rotatably mounted inside the pressure vessel, for example. Even further, in some embodiments, the apparatus comprises an autoclave.

In other embodiments, the invention also provides various apparatuses for treating material that may include combination of a pressure vessel having at least one opening to feed material into the pressure vessel, a door to close the opening of the pressure vessel, a pressure regulating system to change pressure inside the pressure vessel, a steam supply system to supply steam inside the pressure vessel, an agitation device to agitate material received in the pressure vessel, a drive mechanism to move the agitation device, and a heater inside the pressure vessel to heat material in the pressure vessel, as another example.

Some such embodiments may further include a drum to hold the material, for example, which may be located within the pressure vessel, and the drive mechanism may rotate the drum. In some such embodiments, the agitation device may be located inside the drum, for example. Further, in some such embodiments, the steam supply system may include a steam supply conduit extending into an inner space of the drum, for example, through an opening at an end of the drum facing away from the opening of the pressure vessel, for instance.

In yet another embodiment, the invention also provides various apparatuses for treating material that may include a pressure vessel having at least one opening capable of being used to feed material into the pressure vessel, combined with a door capable of closing the opening of the pressure vessel, and an agitation device capable of agitating material received in the pressure vessel, as examples. In various such embodiments, the agitation device may include a drum, which may be rotatably arranged inside the pressure vessel so as to be rotatable in relation to the pressure vessel, for example, and which has an inner space capable of receiving material that may be introduced into the pressure vessel via the opening of the pressure vessel. In a number of such embodiments, the drum may have a wall capable of preventing material received in the inner space of the drum from falling into an interspace between the drum and the pressure vessel as the drum rotates in relation to the pressure vessel. Further, in various such embodiments, the agitation device may include at least one agitation blade mounted on an inner side of the wall of the drum so as to act on material received in the inner space of the drum as the drum rotates in relation to the pressure vessel. The apparatus may further include a drive mechanism capable of rotating the drum in relation to the pressure vessel, and the at least one agitation blade may be screw-shaped. Similar to some previously-described embodiments, such a blade may be arranged to move material received in the inner space of the drum forward away from the opening of the pressure vessel when the drum is rotated by the drive mechanism in a first direction, and the at least one agitation blade may be arranged to move material received in the inner space of the drum backward towards the opening of the pressure vessel when the drum is rotated by the drive mechanism in a second direction opposite the first direction, for example.

In some such embodiments, such an apparatus may include a steam supply conduit, for example, extending into the inner space of the drum through an opening at an end of the drum facing away from the opening of the pressure vessel. Further, in some such embodiments, the drum rests on rollers which are rotatably mounted inside the pressure vessel, for example. In addition, various other embodiments of the invention are also described herein.

BRIEF DESCRIPTION OF THE DRAWINGS

FIG. 1 is a partly-cut side view of an apparatus with an inlet arrangement for steam and compressed air shown in a detail enlargement, which is an example of an embodiment;

FIG. 2 is a cross-sectional view along the line II-II in FIG. 1;

FIG. 3 is a cross-sectional view along the line III-III in FIG. 1;

Figure 4:
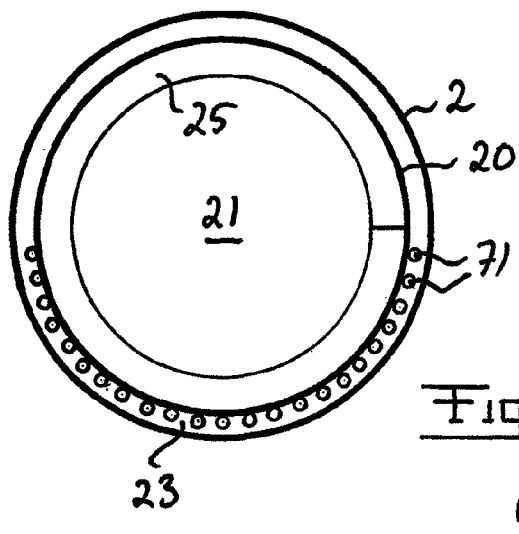
FIG. 4 is a cross-sectional view along the line IV-IV in FIG. 1.

The drawings illustrate, among other things, various examples of embodiments of the invention, and certain examples of characteristics thereof. Different embodiments of the invention include various combinations of elements shown in the drawings, described herein, known in the art, or a combination thereof, for instance.

DETAILED DESCRIPTION OF EXAMPLES OF EMBODIMENTS

FIG. 1 illustrates an apparatus 1, which is an example of an embodiment for treating material, for instance material in the form of waste (e.g., household garbage). In the embodiment illustrated, apparatus 1 includes an elongated pressure vessel 2, which is secured (non-rotating) to a support structure 3 in the form of a frame or a base, as examples. In this embodiment, pressure vessel 2 has an opening 4 at one end capable of being used to feed material into and discharge material out of pressure vessel 2. Thus, opening 4 constitutes an inlet opening for material to be treated in the pressure vessel and also an outlet opening for material treated therein.

Figure 5:
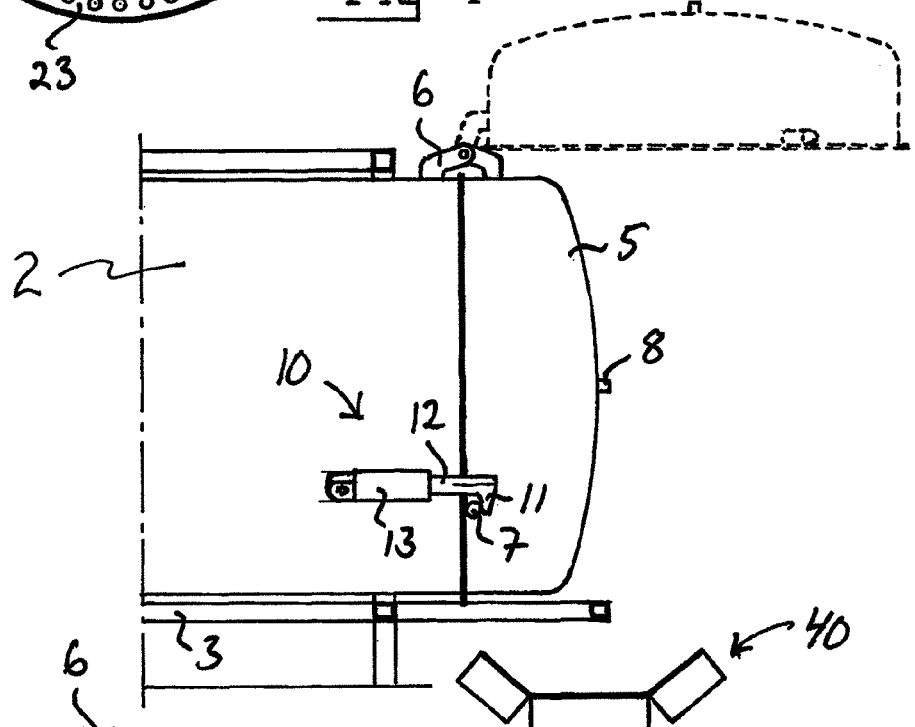
FIG. 5 is a side view of a part of the apparatus of FIG. 1 with a closed door.
Figure 6:
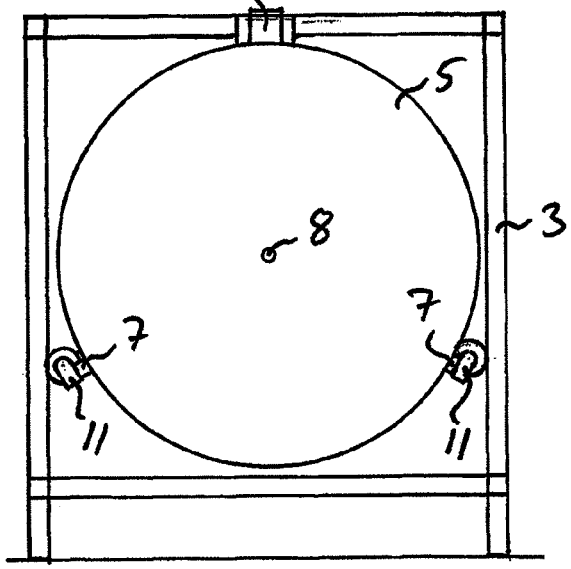
FIG. 6 is a front view of the apparatus of FIG. 1 with the closed door.

In the embodiment illustrated, opening 4 is closable by means of pressure-tight door 5, which in the illustrated example, is hingedly mounted to the pressure vessel 2 via hinge 6. In the embodiment shown, apparatus 1 includes hydraulically, pneumatically or electrically actuated clamps 10 (see FIGS. 5-7), as examples, for clamping door 5 (e.g., tightly enough to form an adequate seal) to pressure vessel 2 when door 5 is in its closed position. In various embodiments, clamps 10 may include one, two, or more clamping members 11 distributed about the opening 4, for example. In the illustrated example, the respective clamping member 11 has the form of a hook, which may be connected to a piston (e.g., at 12) of a hydraulic cylinder so as to be displaceable between a locking position (see FIG. 5), in which the clamping member 11 is in engagement with pin 7 extending from door 5 so as to force the rim of the door into pressure-tight engagement with pressure vessel 2, and an unlocking position (not shown), in which the clamping member 11 is out of engagement with the associated pin 7 so as to allow the door 5 to be moved from its closed position (indicated by continuous lines in FIG. 5) to its open position (indicated by broken lines in FIG. 5). In various embodiments, clamps 10 may be secured to the pressure vessel 2 or to the support structure 3, as examples. In other embodiments, clamps (e.g., similar to 10) may be different than here illustrated.

As an alternative to what is shown, in some embodiments, the pressure vessel may be provided with an inlet opening at one end to feed material into the pressure vessel and an outlet opening at the opposite end to discharge material out of the pressure vessel, with a closable door (e.g., similar to door 5) at each opening, as another example.

In the embodiment shown, apparatus 1 further includes an agitation device to agitate, or capable of agitating, material received in the pressure vessel 2. The agitation device, in this embodiment, includes drum 20 (e.g., shown in FIGS. 1 to 4), which is rotatably arranged inside pressure vessel 2 so as to be rotatable in relation to the pressure vessel. In this particular embodiment, drum 20 has an inner space 21 capable of receiving material that is introduced into pressure vessel 2 via the opening 4 of the pressure vessel. Further, in this embodiment, drum 20 has a cylindrical wall 22 capable of preventing or designed to prevent material received in the inner space 21 of drum 20 from falling into the interspace 23 between drum 20 and pressure vessel 2 as the drum rotates in relation to the pressure vessel. In other embodiments, a drum may have a different shape besides cylindrical, such as spherical, conical, or frustoconical, as examples. In this particular embodiment, drum 20 is rotatable about its longitudinal axis and may be arranged, as illustrated, with its longitudinal axis extending in a horizontal or at least essentially horizontal (or approximately horizontal) horizontal direction. In a number of embodiments, a bottom surface of a drum may be horizontal or approximately horizontal, for example. In the embodiment illustrated, drum 20 rests on rollers 24, which are rotatably mounted inside the pressure vessel 2, for example, as illustrated in FIGS. 1 and 3. In the illustrated example, the rollers 24 are idle rollers arranged in pairs at two or more locations along the drum, for example.

In the embodiment shown, drum 20 is rotated in relation to pressure vessel 2 by means of suitable drive mechanism 30 (see FIGS. 1 and 2). In the illustrated example, drive mechanism 30 includes a reversible motor 31, for instance a hydraulic motor, arranged inside pressure vessel 2. In this particular embodiment, motor 31 drives a rotatably mounted gearwheel 32 via a gear box or reduction gear 33. Gear wheel 32, in this embodiment, engages with a gear ring 34, which is fixedly secured to the outer side of drum 20 and surrounds the drum. The gear ring 34 and thereby the drum 20, is rotated in the desired direction, in this embodiment, when the gear wheel 32 is put into rotation by the motor 31. In other embodiments, drive mechanism (e.g., similar to 30) may be designed in other manners than here illustrated, capable of rotating the drum (e.g., 20). In other embodiments, for example, the drum (e.g., 20) may be rotated by an electric motor, using a chain or belt drive, using a shaft that passes thorough the pressure vessel (e.g., 2) wall, or the like, as examples.

In the embodiment shown, the agitation device further includes at least one agitation blade 25 mounted along the inner side of the cylindrical wall 22 of drum 20, for example, so as to act on material received in the inner space 21 of the drum as the drum rotates in relation to the pressure vessel 2. The agitation blade 25, in this embodiment, is fixed to the cylindrical wall 22 of drum 20 so as to rotate together with the drum and, in the embodiment illustrated, blade 25 extends in a helical path along the cylindrical wall 22, i.e., in the axial or longitudinal direction of the drum 20, and is suitably a screw-shaped blade. The agitation blade 25, in the embodiment illustrated, may extend continuously along the cylindrical wall 22 from one end to the other end thereof, for example, or may be divided into separate parts with intermediate gaps, as another example.

In the particular embodiment illustrated, agitation blade 25 is arranged to move material received in the inner space 21 of drum 20 forward away from the opening 4 of the pressure vessel when the drum 20 is rotated by the drive mechanism 30 in a first direction, and backward towards the opening 4 when drum 20 is rotated by the drive mechanism in a second direction opposite the first direction. Thus, drum 20 is rotated in the first direction when material is fed into the inner space 21 of the drum via the opening 4 and in the opposite second direction when the material is to be discharged out of the opening 4.

Figure 7:
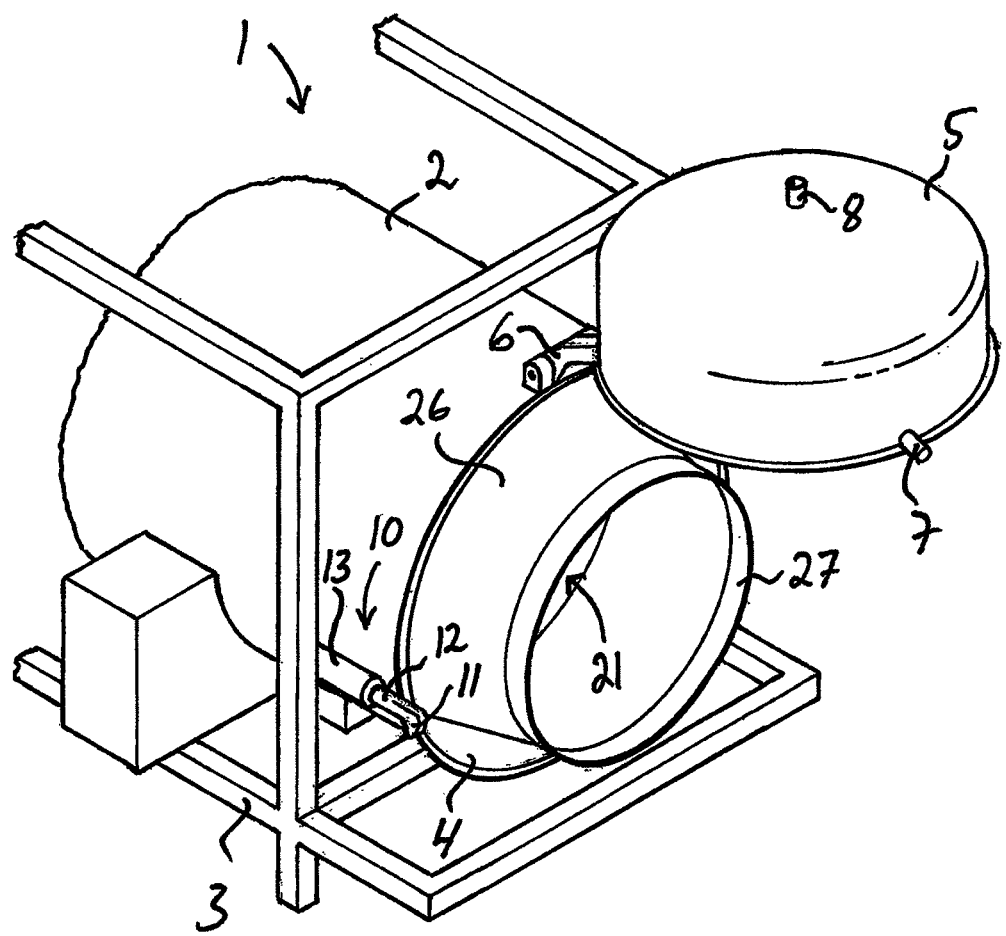
FIG. 7 is an isometric view of a part of the apparatus of FIG. 1 with the door open.

In the embodiment shown, drum 20 has an open end 26 projecting through the opening 4 of the pressure vessel 2, as illustrated in FIGS. 1 and 7. Thus, this end 26 of the drum extends beyond the corresponding end of the pressure vessel 2 and material may consequently be fed into and discharged out of the inner space 21 of the drum without detrimentally falling down onto the bottom of the pressure vessel 2. In this particular embodiment, end 26 of drum 20 is suitably tapered towards opening 27 thereof, as illustrated in FIGS. 1 and 7. In this embodiment, door 5 is arranged to close or is capable of closing opening 4 of pressure vessel 2 as well as opening 27 of drum 20 and has a part 5a (shown in FIG. 1) arranged to extend into the opening 27 of drum 20 when door 5 is in its closed position. A small gap 28, in the embodiment illustrated, is suitably provided between the rim of opening 27 and door 5 when the door is in its closed position, in the embodiment illustrated, so as to allow drum 20 to rotate freely in relation to the door.

In some embodiments, a conveyor 40, for instance such as a belt conveyor, may be arranged under pressure vessel 2 below opening 27 of drum 20 (see FIG. 5) so as to receive material discharged out of the drum and carry this material away, for example, for further processing. Once treated, material may be screened, sorted, dried, or further treated in another manner, as examples. Treated material may be used to make bio fuels, used as compost, burned as a fuel, or buried in a land fill, as examples.

In the embodiment illustrated, apparatus 1 further includes pressure regulating system 50 (e.g., shown in the detail view of FIG. 1) to change or generate a pressure inside pressure vessel 2, for example, above or below that of the atmosphere. In the embodiment shown, inner space 21 of drum 20 is in communication (e.g., via gap 28) with interspace 23 between the drum and the pressure vessel 2 so as to secure that there is no pressure difference between the inner side and the outer side of the drum. The pressure regulating system 50 may be arranged to generate an overpressure (e.g., a pressure above that of the atmosphere, for example, 70 to 80 pounds per square inch) inside the pressure vessel 2 by feeding compressed air and/or compressed steam into the pressure vessel. In some embodiments, pressure regulating system 50 may be arranged to generate vacuum inside the pressure vessel by exhausting air out of the pressure vessel by suction. Thus, in various embodiments, pressure regulating system 50 may include an air compressor, a source of pressurized steam such as a boiler, a vacuum pump, or a combination thereof, as examples. In a number of embodiments, pressure regulating system 50 may include various piping, conduits, tubing, hoses, control devices, pressure measuring devices, valves, seals, passageways through the wall of the pressure vessel, or a combination thereof, as examples.

In the illustrated example, pressure regulating system 50 includes an air supply conduit 51 extending into the inner space 21 of the drum through a pressure-tight lead-through 52 at the closed end of the pressure vessel 2 and through a central opening 29 at the inner end of the drum 20, as illustrated in the detail enlargement of FIG. 1. An air outlet nozzle 53, in the embodiment shown, is provided in the inner space 21 of the drum at the end of the air supply conduit 51. In other embodiments, pressure regulating system 50 may differ. In some embodiments, for example, compressed air, steam, or both, may be delivered to interspace 23 between drum 20 and pressure vessel 2, and may enter drum 20 via gap 28, for instance.

In the embodiment shown, apparatus 1 further includes steam supply system 60, for example, to supply steam into the inner space 21 of drum 20. In the illustrated example, steam supply system 60 includes a steam supply conduit 61 extending into the inner space 21 of drum 20 through a pressure-tight lead-through 62 at the closed end of pressure vessel 2 and through opening 29 at the inner end of the drum 20, as illustrated in the detail enlargement of FIG. 1. In this embodiment, steam outlet nozzle 63 is provided in the inner space 21 of drum 20 at the end of the steam supply conduit 61. In other embodiments, steam supply system 60 may differ. In various embodiments, one or several steam outlets may be arranged in pressure vessel 2, as examples. In some embodiments, one or several steam outlets may be arranged in door 5, for instance. In the illustrated example, door 5 is provided with such an outlet 8, for example. In various embodiments, steam supply system 60 may also include a steam source, such as a boiler, for example.

In the embodiment illustrated, apparatus 1 further includes heater 70 to heat material received in the inner space 21 of drum 20. The temperature in the inner space 21 of the drum may be controlled by means of heater 70 so as to achieve a desired temperature level suitable for the material treatment. In the illustrated example, heater 70 includes heating members 71 (see FIGS. 1 and 4) in the form of interconnected water conduits extending along a part of the drum 20 in the interspace 23 between the drum and the pressure vessel 2. These heating members 71, in this particular embodiment, are connected to a hot water supply (not shown) via a feeding conduit 72 extending through a pressure-tight lead-through 73 in pressure vessel 2 and a return conduit 74 extending through a pressure-tight lead-through 75 in the pressure vessel. In other embodiments, heater 70 may contain steam or products of combustion from a remote burner, may be an electrical resistance heater, or may be or include a burner, as other examples. In some embodiments, a heater may include heating members or a burner located on the outside of the pressure vessel, for example. In particular embodiments, the heater may include another suitable type of heating members.

In certain embodiments, apparatus 1 may constitute or comprise an autoclave, particularly an autoclave for treating waste or garbage, for example. In various embodiments, the invention is not in any way restricted to the particular embodiments described above. On the contrary, many possibilities to modifications thereof may be apparent to a person with ordinary skill in the art without departing from the basic idea of the invention as defined in the appended claims.

What is claimed is:

1. An apparatus for treating material, the apparatus comprising:
   a non-rotating pressure vessel having at least one opening to feed the material into the pressure vessel;
   a door to close the at least one opening of the pressure vessel;
   a pressure regulating system to change pressure inside the pressure vessel; and
   an agitation device to agitate the material received in the pressure vessel;
   wherein the agitation device comprises a drum, which is rotatably arranged inside the pressure vessel so as to be rotatable in relation to the pressure vessel and which has an open end to an inner space for receiving the material that is introduced into the pressure vessel via the at least one opening of the pressure vessel, the drum having a cylindrical wall designed to prevent the material received in the inner space of the drum from falling into an interspace between the drum and the pressure vessel as the drum rotates in relation to the pressure vessel;
   wherein the agitation device comprises at least one agitation blade mounted on an inner side of the cylindrical wall of the drum so as to act on the material received in the inner space of the drum as the drum rotates in relation to the pressure vessel; and
   wherein the apparatus further comprises a drive mechanism comprising a motor that is located inside the pressure vessel in the interspace between the drum and the pressure vessel that rotates the drum in relation to the pressure vessel.

2. The apparatus of claim 1 wherein the at least one agitation blade extends in a helical path along the cylindrical wall of the drum.

3. The apparatus of claim 1 wherein the motor is a reversible hydraulic motor.

4. The apparatus of claim 1 wherein the at least one agitation blade is arranged to move the material received in the inner space of the drum away from the at least one opening of the pressure vessel when the drum is rotated by the drive mechanism in a first direction, and wherein the at least one agitation blade is arranged to move the material received in the inner space of the drum towards the at least one opening of the pressure vessel when the drum is rotated by the drive mechanism in a second direction opposite the first direction.

5. The apparatus of claim 1 wherein the drum has a longitudinal axis and the drum is arranged with the longitudinal axis extending in a horizontal or at least approximately-horizontal direction.

6. The apparatus of claim 1 wherein the drum has an open end projecting through the at least one opening of the pressure vessel, and the door is arranged to close the at least one opening of the pressure vessel as well as the open end of the drum.

7. The apparatus of claim 6 wherein the door has a part arranged to extend into the open end of the drum when the door is closed.

8. The apparatus of claim 1 wherein the apparatus comprises hydraulically, pneumatically or electrically actuated clamps for clamping the door to the pressure vessel when the door is closed.

9. The apparatus of claim 1 wherein the apparatus comprises a heater to heat the material received in the inner space of the drum.

10. The apparatus of claim 9 wherein the heater comprises at least one heating member arranged in the interspace between the drum and the pressure vessel.

11. The apparatus of claim 1 wherein the apparatus comprises a steam supply system to supply steam into the inner space of the drum.

12. The apparatus of claim 11 wherein:
the pressure vessel further comprises a closed end opposite the at least one opening of the pressure vessel;
the drum further comprises an inner end located within the closed end of the pressure vessel;
the steam supply system comprises a steam supply conduit extending into the inner space of the drum through a central opening at the inner end of the drum at the closed end of the pressure vessel.

13. The apparatus of claim 1 wherein the drum rests on rollers which are rotatably mounted inside the pressure vessel.

14. The apparatus of claim 1 wherein the apparatus comprises an autoclave.

15. An apparatus for treating material, the apparatus comprising:
a pressure vessel having at least one opening to feed the material into the pressure vessel;
a door to close the at least one opening of the pressure vessel;
a pressure regulating system to change pressure inside the pressure vessel;
a steam supply system to supply steam inside the pressure vessel;
an agitation device to agitate the material received in the pressure vessel;
a drum rotatably arranged inside the pressure vessel that is rotatable in relation to the pressure vessel and which has an open end and an inner space for receiving the material that is introduced into the pressure vessel via the at least one opening of the pressure vessel, the drum having a wall to prevent the material received in the inner space of the drum from falling into an interspace between the drum and the pressure vessel as the drum rotates in relation to the pressure vessel;
a drive mechanism to move the agitation device; and
a heater inside the pressure vessel to heat the material in the pressure vessel; and
wherein the door has a part arranged to extend into the open end of the drum when the door is closed.

16. The apparatus of claim 15 wherein the drive mechanism comprises a motor located within the pressure vessel, and wherein the drive mechanism rotates the drum and the agitation device is located inside the drum.

17. The apparatus of claim 16 wherein:
the pressure vessel further comprises a closed end opposite the at least one opening of the pressure vessel;
the drum further comprises an inner end located within the closed end of the pressure vessel;
the steam supply system comprises a steam supply conduit extending into the inner space of the drum through a central opening at the inner end of the drum at the closed end of the pressure vessel.

18. An apparatus for treating material, the apparatus comprising:
A non-rotating pressure vessel having at least one opening capable of being used to feed the material into the pressure vessel and a closed end opposite the at least one opening;
a door capable of closing the at least one opening of the pressure vessel;
an agitation device capable of agitating the material received in the pressure vessel;
wherein the agitation device comprises a drum, which is rotatably arranged inside the pressure vessel so as to be rotatable in relation to the pressure vessel and which has an inner space capable of receiving the material that is introduced into the pressure vessel via the at least one opening of the pressure vessel, the drum having a wall capable of preventing the material received in the inner space of the drum from falling into an interspace between the drum and the pressure vessel as the drum rotates in relation to the pressure vessel, and an inner end located within the closed end of the pressure vessel;
wherein the agitation device comprises at least one agitation blade mounted on an inner side of the wall of the drum so as to act on the material received in the inner space of the drum as the drum rotates in relation to the pressure vessel;
wherein the apparatus further comprises a drive mechanism capable of rotating the drum in relation to the pressure vessel; and
wherein the at least one agitation blade is screw-shaped and is arranged to move the material received in the inner space of the drum away from the at least one opening of the pressure vessel when the drum is rotated by the drive mechanism in a first direction, and wherein the at least one agitation blade is arranged to move the material received in the inner space of the drum towards the at least one opening of the pressure vessel when the drum is rotated by the drive mechanism in a second direction opposite the first direction; and
the apparatus further comprises a steam supply conduit extending into the inner space of the drum through an opening at the inner end of the drum at the closed end of the pressure vessel.

19. The apparatus of claim 18 further comprising a drive mechanism comprising a motor located inside the pressure vessel in the interspace between the drum and the pressure vessel that rotates the drum in relation to the pressure vessel.

20. The apparatus of claim 19 wherein the door has a part arranged to extend into the open end of the drum when the door is closed.

* * * * *